United States Patent [19]

Sunano et al.

[11] Patent Number: 4,713,646
[45] Date of Patent: Dec. 15, 1987

[54] GAS SENSOR AND METHOD OF PRODUCING THE SAME

[75] Inventors: Naomasa Sunano, Akashi; Naotatsu Asahi, Katsuta; Toshio Yoshida, Kasukabe, all of Japan

[73] Assignees: Shinyei Kaisha, Hyogo; Hitachi, Ltd., Tokyo, both of Japan

[21] Appl. No.: 748,198

[22] Filed: Jun. 24, 1985

[51] Int. Cl.$^4$ ................................................. H01L 7/00
[52] U.S. Cl. .......................................... 338/34; 427/34; 29/592 R; 29/610 R
[58] Field of Search ............... 338/34, 35, 22 R; 219/121 PL; 29/610 SG, 592 R, 610 R; 73/23, 27 R; 123/393, 440; 427/34

[56] References Cited

U.S. PATENT DOCUMENTS

| | | | |
|---|---|---|---|
| 3,197,335 | 7/1965 | Leszynski | 29/610 SG |
| 4,299,859 | 11/1981 | Romine | 427/34 |
| 4,324,761 | 4/1982 | Harris | 338/34 X |
| 4,377,801 | 3/1983 | Weber | 338/34 |
| 4,505,947 | 3/1985 | Vukanovic et al. | 219/121 PL |
| 4,535,316 | 8/1985 | Wertheimer et al. | 338/34 |
| 4,536,640 | 8/1985 | Vukanovic | 219/121 PL |
| 4,580,439 | 4/1986 | Manaka | 338/34 X |

FOREIGN PATENT DOCUMENTS

| | | |
|---|---|---|
| 0007621 | 7/1979 | European Pat. Off. |
| 147170 | 7/1985 | European Pat. Off. ...... 219/121 PL |
| 55-18922 | 2/1980 | Japan . |
| 55-51764 | 4/1980 | Japan . |
| 55-124059 | 9/1980 | Japan . |
| 55-124058 | 9/1980 | Japan . |
| 55-140138 | 11/1980 | Japan . |
| 56-164948 | 12/1981 | Japan . |
| 2003272 | 3/1979 | United Kingdom . |

Primary Examiner—E. A. Goldberg
Assistant Examiner—M. M. Lateef
Attorney, Agent, or Firm—Antonelli, Terry & Wands

[57] ABSTRACT

A gas sensor includes a pair of electrodes printed on an electrically insulating substrate, a sensitive layer deposited on tip portions of the electrodes and a part of the substrate adjacent to the tip portions and bridging the space between the electrodes at the tip portion, and a protective film deposited on the electrodes and a part of the substrate adjacent to the tip portion so that a part of each electrode covered with the sensitive layer is free of the protective film. The sensitive layer is formed by depositing titanium oxide by plasma spraying on the substrate, and then heat-treating the deposited titanium oxide, so as to provide a diffusion reactive layer between the sensitive layer and the substrate and to form fine grooves on the surface of the sensitive layer.

26 Claims, 12 Drawing Figures

950°C OR BELOW

FIG. 6B

1100°C OR ABOVE

FIG. 7A

— SENSITIVE BODY
— DIFFUSION LAYER
— SUBSTRATE

FIG. 7B

— SENSITIVE BODY
— DIFFUSION LAYER
— SUBSTRATE (b) SENSITIVE PORTION

GAS SENSOR AND METHOD OF PRODUCING THE SAME

BACKGROUND OF THE INVENTION

1. Field of the Invention

This invention relates to a gas sensor using titanium oxide ($TiO_2$) as a sensitive member and to a method of producing the gas sensor. More particularly, the present invention relates to a gas sensor having a layer which is used as a sensor sensitive member and has a lot of fine voids formed in the surface, and to a method of producing the gas sensor.

2. Description of the Prior Art

A gas sensor measures the concentration of oxygen, hydrocarbons, alcohols, fumes, humidity, and the like, in an atmosphere. Generally, the gas sensor has a sensitive member and a pair of electrodes on an electrically insulating substrate. A part of the surface of the sensitive member is sometimes covered with a protective film. Titanium oxide ($TiO_2$) is known as one of the materials for the sensitive member.

Titanium oxide is an n-type semiconductor. This titanium oxide has a property such that its resistance value increases with an increasing oxygen concentration in an atmospheric gas. Accordingly, a proposal has been made to use titanium oxide as the sensitive member of the gas sensor by utilizing this property.

An oxygen sensor is disclosed in Japanese Patent Laid-Open No. 164948/1981 as an example of the conventional titanium oxide type sensors. The oxygen sensor is produced by adding 0.5 to 20 mol % of silicon oxide to 99.5 to 80 mol % of titanium dioxide, adding an organic solvent to the mixture to turn it to a slurry, shaping the slurry to a sheet and putting electrodes on both surfaces of the sheet.

However, this gas sensor is a sintered product and impurities from silicon dioxide or from the organic solvent will mix, so that the response of the sensor is slow. It is known, on the other hand, how to improve the response of the gas sensor by lowering the sintering temperature thereby making the sensitive member porous in order to improve the response. However, this method involves another problem in that it reduces the mechanical strength of the sensitive member. When a sensor produced by this method is used for measuring the concentration of an exhaust gas of automobiles or for controlling the combustion of heating equipment, the durability of the gas sensor is not sufficient because of thermal stress in the thermal cycle during repeated use of the sensor at temperatures ranging from normal temperature to close to 1,100° C. and the stress due to mechanical vibration.

To improve the strength and response of the gas sensor, an invention is disclosed in Japanese Patent Laid-Open No. 124059/1980 in which an electrode—metal oxide (as the sensitive member)—electrode—protective film are sequentially disposed on a heat-resistant insulating substrate, and titanium dioxide is used as the metal oxide. This invention makes it possible to reduce the thickness of the sensitive member because it is formed by screen printing, and to improve the response by reducing the diffusion distance of the detected gas inside the sensitive member. However, the problem of the mixture of impurities from the organic solvent remains unsolved. Moreover, this prior art invention plasmasprays spinel such s $MgO.Al_2O_3$ as a gas permeable protective film on the surface of the sensitive member in order to improve the durability or response of the sensor.

To improve the response of an oxygen sensor element consisting of titanium dioxide, Japanese Patent Laid-Open No. 41764/1980 discloses a sensor in which 0.02 to 20 mol % of the elements of the Group V of the Periodic Table such as antimony (Sb), niobium (Nb), tantalum (Ta) and the like and 0.02 to 20 mol % of platinum (Pt) are added to a sintered body consisting of titanium dioxide as the principal component. This sensor, too, is a sintered body. The durability of the sensor can be improved by elevating the sintering temperature in the sintering process, but the response is reduced. If the sintering temperature is lowered, the response can be improved, but the durability will be reduced and the problem of mixture of impurities will occur.

If Sb, Nb, Ta or the like is added to titanium dioxide, the internal resistance of the sensor will change and its response will be reduced in the course of use of the sensor for an extended period.

Japanese Patent Laid-Open No. 124058/1980 discloses another type of sensor. In accordance with this prior art, titanium dioxide used is in the form of particles having a maximum size of 100Å which are precipitated as a gel-like aqueous solution to form a flake-like anatase structure. The sensor is shaped from this structure in such a fashion that its surface area is at least 3 $m^2/g$. The sensor of this prior art is not substantially different from the sensors of the type described already in its response and durability brought forth by sintering, but since the sensor is composed of only the sensitive member, its mechanical strength is low.

Japanese Patent Laid-Open No. 140138/1980 discloses an invention in which the titanium oxide sintered body is a porous body having a relative density of from 0.7 to 0.5, the average particle size of titanium oxide is from 1 to 5 $\mu$m and partial fusion is caused between the particles to improve the response. Since the titanium oxide sintered body is produced by the greensand method, this prior invention has low durability. When the sensitive member is porous as a whole and is disposed on an insulating substrate, the diffusion distance in the adsorption and desorption of a detected gas becomes great. Therefore, when a gas concentration changes abruptly, tailing occurs. To minimize tailing, Japanese Patent Laid-Open No. 18922/1980 discloses an invention in which a 50 to 100 $\mu$m thick powdery paste containing a transition metal oxide is deposited by screen printing on an insulating substrate made of ceramics, and after sintering, MgO and $Al_2O_3$ are further coated thereon. In this case, too, the problems of the mixture of impurities from the paste and the tailing phenomenon resulting from $MgO.Al_2O_3$ coating remain unsolved.

As described above, gas sensors using metal oxides, particularly titanium oxide, have been well known. All the known titanium oxide type gas sensors covert fine powder as the raw material to a slurry, and sinter the slurry to form the sensitive member. The response of the titanium oxide gas sensor becomes higher with a decreasing particle diameter of the starting fine particles. However, when the sensitive member is molded by sintering as in the prior art described above, the fine particles of titanium oxide are mutually diffused and fused in the subsequent sintering process, thereby forming the sensitive member. The mechanical strength of the resulting sensitive member is significantly affected by the area of this interdiffusion. The area of interdiffusion becomes greater with a higher sintering temperature, and the strength can be improved, too. As this area becomes greater, however, the neck portions become smaller which cause the resistance change due to the adsorption and desorption of the gas, so that the response is reduced. If a trace element is added in order to promote sintering and thus to improve the response, the resistance value of the sensitive member will change with time in the course of a long period so that the gas sensing temperature will drop.

A method which sinters a gas sensitive member on a ceramic substrate has also been known. In this case, the state of close contact of the gas sensitive member with the substrate becomes a factor that determines the durability of the sensitive member. To improve the close contact and strength between titanium dioxide and the ceramic substrate, it is desired that interdiffusion be caused between the ceramic substrate and titanium dioxide. In accordance with the conventional sintering method, however, the sintering temperature must be raised as described already, but interdiffusion of the sensitive member develops with the temperature rise and with the progress of the reaction, so that the response drops eventually.

SUMMARY OF THE INVENTION

An object of the present invention is to provide a gas sensor which can improve both the response (that is, response speed) of a sensitive member and its durability in the course of repeated use for a long period, and can prevent tailing, and also a method of producing such a gas sensor.

In a gas sensor of the type in which a plurality of electrodes are arranged on an electrically insulating substrate and a sensitive member is electrically connected between the electrodes, the present invention is characterized in that the sensitive member includes a thermally sprayed titanium oxide layer having fine grooves or fine pores in its surface portion, and has a reactive phase between the layer and the substrate.

In the gas sensor of the present invention described above, a stoichiometrically metastable layer of $TiO_{2-x}$ is formed on the electrically insulating substrate by thermal spraying such as plasma spraying titanium oxide ($TiO_2$) on the substrate in an atmosphere including hydrogen gas, and the layer is then heat-treated in an atmosphere including oxygen in order to form fine grooves or pores at the surface portion of the layer and to form stabilized titanium oxide ($TiO_2$).

The stoichiometrically metastable layer of $TiO_{2-x}$ and the substrate react with each other at the time of the thermal spraying and at the heat treatment conducted after that to form a diffusion reactive layer at their boundary. The lower limit of the heat-treatment temperature is 1000° C. and the upper limit is little less than the melting point of the substrate and the titanium oxide. The structure of the reactive layer formed between the substrate and the titanium oxide is solid solution of alumina ($Al_2O_3$) and titania or a compound oxide such as $Al_2TiO_5$ when the substrate is alumina.

The thickness of the reactive layer is preferable to be 0.1-5 $\mu$m, particularly preferable to be 0.8-1.2 $\mu$m.

The thickness of the reactive layer is controlled by controlling thermal spraying and heat treatment conditions.

To improve the response and durability of the titanium oxide type gas sensor and to prevent tailing, it is important that a thin layer of the sensitive member be formed on the electrically insulating substrate and its surface be made porous.

The electrically insulating substrate is preferably as thin as possible so long as sufficient mechanical strength is secured. In other words, the thicker the substrate, the greater becomes the heat capacity. Therefore, the heat change causes a thermal gradient and thermal stress, as well, and the resistance change of the sensitive member exerts adverse influences upon detection sensitivity. Preferable thickness of the substrate is 0.4-0.6 mm.

From the aspect of durability, it is preferred for the gas sensor that the substrate and the sensitive member are in close and strong contact with each other. From the aspect of the response speed and of tailing, it is preferred to make the sensitive member of titanium oxide small in thickness so that a gas diffusion distance will be short, and to make the particle size of the titanium oxide small to get a large surface area of the sensitive member. As a result of intensive study of te various methods of producing such a gas sensor, the inventors of the present invention have found that it is effective to bring the titanium oxide into a close contact with the electrically insulating substrate by plasma spraying in an atmosphere including hydrogen gas. The inventors have found also that the surface portion of the layer can be made extremely porous with fine grooves or pores formed therein and large in the contact area between the sensitive member and a combustion gas thereby to improve the response speed, if the titanium oxide layer is formed in an unstable state, that is, in a form of $TiO_{2-x}$, while great internal stress remains, on the substrate, and titanium oxide is thereafter stabilized by the subsequent heat-treatment. The present invention is completed on the basis of these findings.

A film forming method suitable for the conditions described above is a thermal spraying method. Among the thermal spraying methods in general, preferred is a method of plasma spraying in an atmosphere including $H_2$ gas. The layer which is formed by plasma-spraying titanium oxide on the substrate becomes $TiO_{2-x}$. If the layer in which titanium oxide is still unstable in the form of $TiO_{2-x}$ is used as the sensor, the oxygen concentration in the layer will change with the passage of time, and the function of the gas sensor will be lost.

The inventors have also examined various methods of stabilizing the internal resistance of the layer, and have found that it can be stabilized by heat-treating the sprayed layer in an oxygen-containing atmosphere. In other words, if the layer is heat-treated in an oxidizing atmosphere, oxygen is diffused through the pores of the thermal sprayed layer and the internal resistance can be stabilized above a certain temperature. If such a stabilized layer is formed, too, the layer thickness is also an important factor that determines the response and the durability of the gas sensor.

The heat-treatment is conducted in an oxygen-containing atmosphere in order to make the unstable $TiO_{2-x}$ into stable $TiO_2$. The heat-treating temperature is preferably 1080° C. or above. Preferably, the particle diameter of titanium oxide as the raw material is from 1 to 60 $\mu$m, and more preferably 5-25 $\mu$m.

The thermal spraying method is preferably plasma spraying and particularly preferred is plasma spraying in the presence of a mixture of argon and hydrogen.

The resulting sprayed layer is preferably from 10 to 100 $\mu$m thick, more preferably 15-60 $\mu$m thick.

The thermal-sprayed layer less than 10 μm thick is short in life because of its consumption due to contact with the combustion gas and the layer more than 100 μm thick is not good in the response speed.

DESCRIPTION OF THE PREFERRED EMBODIMENT

Figure 1:
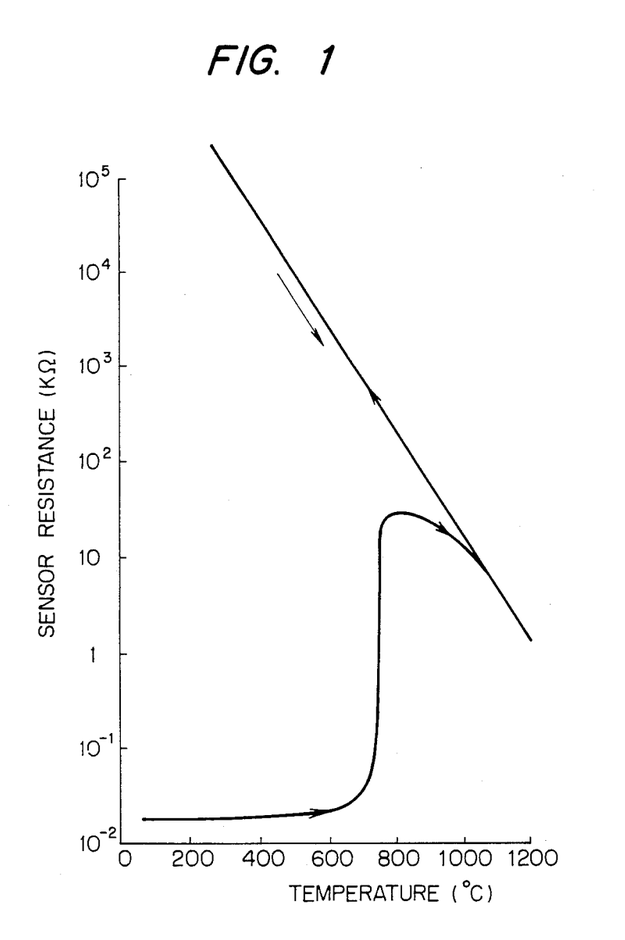
FIG. 1 is a diagram showing the relation between the sensor resistance and the heat-treating temperature of a sprayed $TiO_2$ sensitive member.

FIG. 1 is a diagram showing the relation between the internal resistance of a layer and a heat-treating temperature when titanium oxide is sprayed in a thickness of 50 μm on a 0.6 mm thick alumina ceramic substrate. The specific resistance of the layer in this case is about $10^{-2} \Omega$. cm. The resistance value as the sensitive member is about 20$\Omega$ at room temperature. When this layer is heat-treated for about one hour in an oxygen-containing atmosphere, its electric resistance drastically increases at 700° C., reaching 20 K$\Omega$ at 800° C. However, the resistance value is not yet stabilized under this state, either. When heat-treatment is made at a temperature above 1,000° C., the resistance value is stabilized as shown in the diagram. At temperature above 1,000° C., the resistance value becomes a function of only the temperature in a predetermined gaseous atmosphere. This is due to the change of $TiO_{2-x}$ to a stable $TiO_2$. When the layer is cooled after being heated, the resistance value does not return along the original curve, rises linearly as shown in FIG. 1, and reaches about $10^7$ K$\Omega$ at room temperature. After that, the resistance value changes linearly to change of temperature. After the layer attains this state, it can be used as the sensitive member of a gas sensor.

Next, an embodiment of the present invention will be given.

Platinum electrodes are disposed by printing on a 0.6 mm thick alumina substrate. Titanium oxide is then coated to a thickness of about 50 μm by plasma spraying at the tip portion of the substrate. Titanium oxide is produced by electromelting and is then pulverized to particle diameters of 5 to 44 μm.

Plasma spraying is effected by mixing 20% hydrogen into argon, generating plasma of a 56 KW output, and charging titanium oxide into the plasma jet to apply it on the alumina substrate at a spraying rate of about 1.5 Kg/h. Thereafter, a spinel type ceramic such as MgO. $Al_2O_3$ or the like (including glass coating) is coated to a thickness of about 70 μm on the electrodes to form a protective film. The plasma spraying condition is the same as that for titanium oxide.

Figure 2:
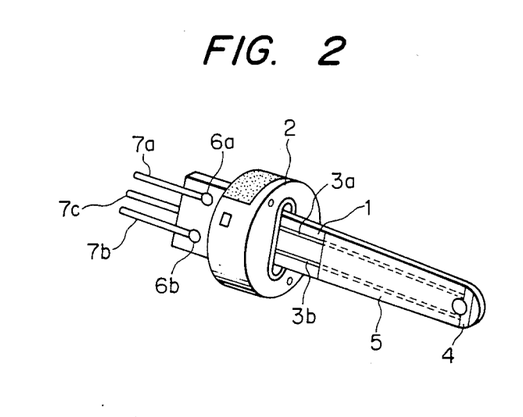
FIG. 2 is a schematic perspective view showing an example of gas sensors in accordnce with the present invention.
Figure 3:
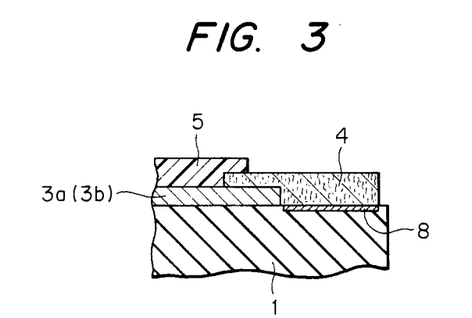
FIG. 3 is a partially enlarged sectional view of the sensitive portion of the gas sensor shown in FIG. 2.

FIG. 2 is a perspective view showing an example of the gas sensor in accordance with the present invention. The gas sensor includes the alumina substrate 1 fitted to, and held by, a fitting-holding jig 2, the electrodes 3a, 3b, the titanium oxide sensitive member 4, the diffusion reactive layer 8 (as shown in FIG. 3) formed between the substrate 1 and the sensitive member 4 and the electrode protective film 5. The terminals of the electrodes 3a, 3b are connected to lead wires 7a, 7b through junctions 6a, 6b.

More definitely, two platinum electrodes 3a, 3b are disposed in parallel with each other on one of the surfaces of the alumina substrate 1 in the longitudinal direction of the substrate 1 by a printing method. One of the ends of each electrode is covered with a coating layer of titanium oxide, and the other end is connected to the lead wire 7a, 7b. The electrode protective film 5 is formed on the electrode on the alumina substrate 1 on the side of the sensitive member 4. A heater wire 7c for heating the sensitive member 4 is disposed on the reverse of the alumina substrate 1.

FIG. 3 shows a partially sectional view of the gas sensor. The tailing is prevented by covering not the whole but part of the upper portions of the electrodes 3a, 3b with the protective film 5, namely, by allowing the end portion of the electrodes 3a, 3b covered with the sensitive member layer 4 to be uncovered with the protective film 5, as shown in FIG. 3.

Figure 4A:
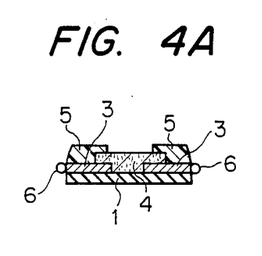
FIGS. 4A and 4B are partially enlarged sectional views each of which shows example of the sensitive portion of the gas sensor.
Figure 4B:
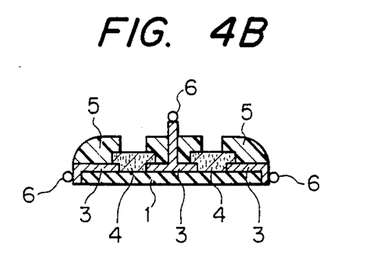

FIGS. 4A and 4B are partially enlarged sectional views showing the sensitive portion of the sensor. FIG. 4A shows only one sensitive member, and FIG. 4B shows an example wherein a plurality of sensitive portions are provided. In these Figures, reference numeral 1 represents the substrate; 3 is the electrode; 4 is the coating of the titanium oxide sensitive member; 5 is the electrode protective film.

Figure 5:
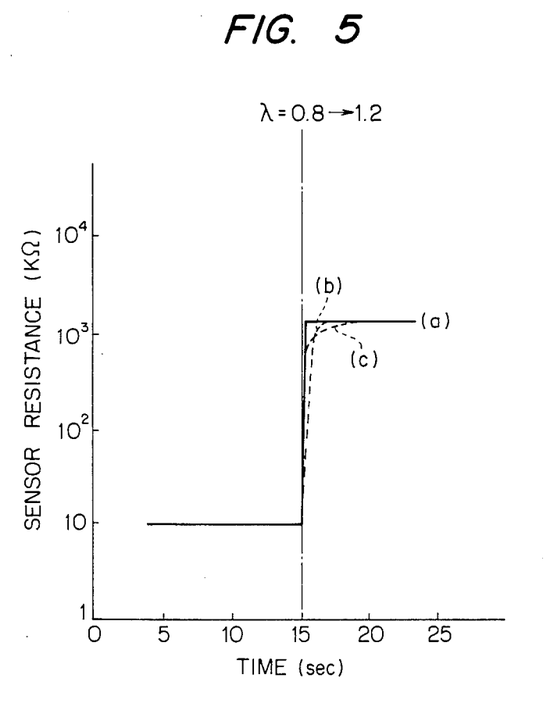
FIG. 5 is a diagram showing the relation between the tailing phenomenon of the gas sensor and the heat-treating condition of the sensitive member.

FIG. 5 shows the air excess ratio in the sensitive member layer and the sensor resistance when such a sensor is used. In the drawing, symbol (a) represents a sensor which is heat-treated at a temperature above 1,100° C. after plasma spraying in the mixture of hydrogen gas and argon gas, (b) represents a sensor heat-treated at 950° C. and (c) represents a sensor which is heat-treated at 1,100° C. or above but in which MgO- .$Al_2O_3$ is coated to cover the whole area of the electrode end portion around the sensitive portion, the sensor resistance changes drastically up to about 90% of the equilibrium value of the resistance of the air excess ratio ($\lambda$) changes from 0.8 to 1.2 as shown at (c), but thereafter changes gradually for a relatively long period before it reaches the equilibrium value, thereby causing tailing. When the heat-treatment is effected at 950° C. at which the gas concentration of the atmosphere reaches a predetermined value depending upon the temperature as shown in FIG. 1, the response tends to drop somewhat as shown in FIG. 5, (c). When the heat-treating temperature is above 1,100° C., the response of the sensor becomes such as shown in FIG. 5, (a), and the sensor resistance follows up the abrupt change of the air excess ratio within an extremely short period of time.

Figure 6A:
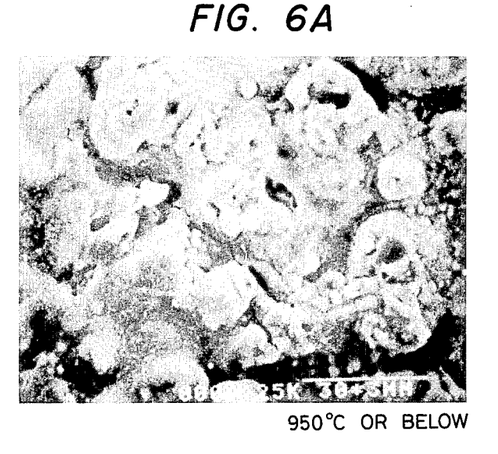
FIGS. 6A and 6B are scanning electron micrographs each showing the surface texture of the sensitive portion.
Figure 6B:
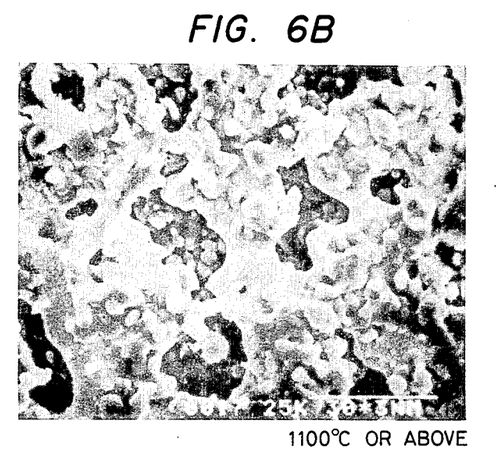

In the manner described above, the difference in response speeds depends on the heat-treating temperature of the sensitive member. To examine this reason, the surface condition of the sensor heat-treated at 1,100° C. or above and that of the sensor heat-treated at 950° C. are observed by a scanning electron microscope with the results shown in FIGS. 6A and 6B. As can be seen from these micrographs, relatively large corrugations exist on the surface of the sensitive portion of the sensor (FIG. 6A), and large continuous cracks exist locally. The corrugations are smaller in the sensitive member (FIG. 6B) heat-treated at 1,100° C. or above than those of the sensor of FIG. 6A, and extremely fine grooves are uniformly dispersed and distributed with gaps of several microns due to recrystallization. Most of these fine grooves are from several $\mu$m to about 20 $\mu$m deep. It has been clarified that such a sensitive portion has a small diffusion distance for the adsorption and desorption of gas, and the sensor whose surface area is increased by the fine corrugations and the fine grooves has a greatly improved response for sensing gas. When the spinel type protective film such as $MgO.Al_2O_3$ is coated in the semiconductor sensor sensitive member of a metal oxide such as titanium oxide as in the conventional sensors, it has been found that the response drops due to the diffusion distance for the gas adsorption and desorption and tailing occurs.

As for the sensor durability, the bonding strength between the substrate and the sensitive member and the adhesion strength of mutual particles inside the sensitive member are associated with the durability. It is possible to cause diffusion sufficient to obtain the required strength by pretreating the substrate and selecting suitable spraying condition in conjunction with the former bonding strength.

Figure 7A:
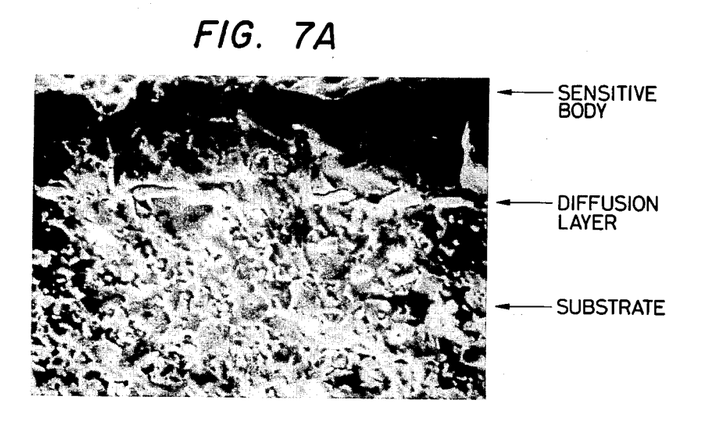
FIGS. 7A and 7B are scanning electron micrographs each showing the sectional textures of the substrate and sensitive portion.
Figure 7B:
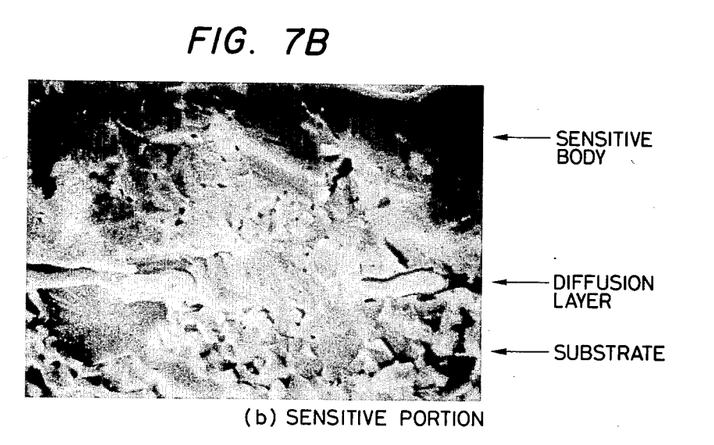

FIGS. 7(A) and 7(B) are SEM micrographs showing the sectional plane between the substrate and the sensor sensitive portion and the bonding state of the sensor sensitive member respectively. It can be seen from FIG. 7A that a mutual diffusion layer is formed by strong bonding between the alumina substrate and titanium oxide. As shown FIG..7B, the interior of the sensitive portion becomes compact and strong mutual diffusion develops.

Next, the response and durability are tested for a sensor which has the same structure as shown in FIG. 4A and which is heat-treated at a temperature of at least 1,100° C. after spraying the sensitive member layer of titanium oxide so as to form fine grooves or holls on the surface.

Figure 8:
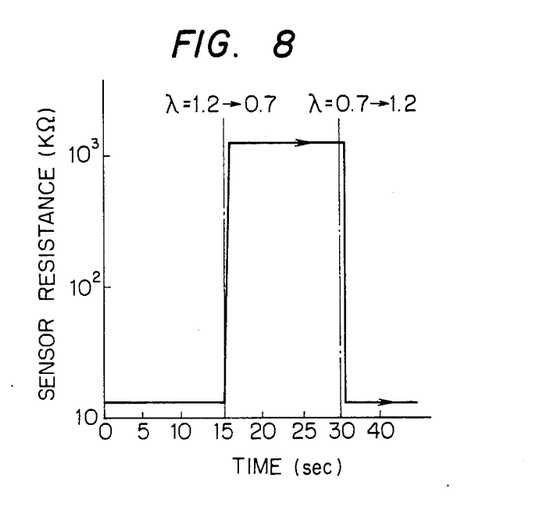
FIG. 8 is a diagram showing the sensor response of the gas sensor in accordance with the present invention.

FIG. 8 is a diagram showing the sensor resistance when the air excess ratio $\lambda$ is changed from 1.2 to 0.7 and is then returned from 0.7 to 1.2. As can be seen from the diagram, the sensor resistance exhibits excellent response to both lean and rich mixtures with respect to the change of the air excess ratio $\lambda$.

Figure 9:
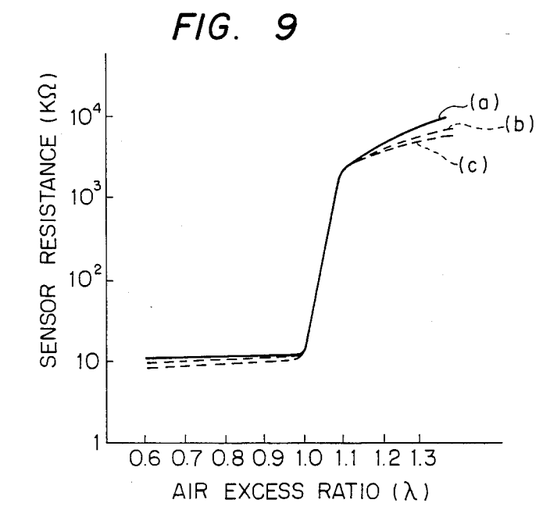
FIG. 9 is a diagram showing the durability of the gas sensor of the present invention.

FIG. 9 is a diagram showing the actually measured values in the durability test of the sensor. Line a in the diagram represents the initial characteristics, line b shows the characteristics when the sensor is held at 1,000° C. for 300 hours and line c shows the relation between the air excess ratio and the sensor resistance when the sensor is held at 1,000° C. for 5,000 hours. As can be understood from the diagram, it is evidenced that the gas sensor of the present invention has extremely high durability.

As described in the foregoing, the present invention can improve the response of the sensitive member, can also improve the durability in the course of repeated use and can prevent tailing.

What is claimed is:

1. In a gas sensor comprising a pair of electrodes juxtaposed with each other on an electrically insulating substrate, a sensitive layer interposed electrically between said electrodes at their one ends, and a protective film covering a part of said sensitive layer and a part of each of said electrodes, the improvement wherein said sensitive layer is a titanium oxide layer formed by spraying titanium oxide on said substrate at a high temperature, wherein a diffusion reactive layer is provided between said titanium oxide layer and said substrate, and wherein the titanium oxide layer has fine grooves or pores in its surface portion.

2. The gas sensor as defined in claim 1, wherein said diffusion reactive layer is 0.1–5 $\mu$m thick.

3. The gas sensor as defined in claim 1, wherein said sensitive layer is 10–100 $\mu$m thick.

4. The gas sensor as defined in claim 1, wherein said sensitive layer has resistance of at least 100 M$\Omega$ in the atmosphere.

5. The gas sensor as defined in claim 1, wherein said protective film is heat-resistant and electrically insulating, and is deposited both on a part of said sensitive layer so that said part of said sensitive layer free of the deposition is wider than the gap between said electrodes, and on a part of each electrode.

6. The gas sensor as defined in claim 1, wherein said protective film is deposited on said electrodes so that a part of one end portion of said each electrode covered with said sensitive layer is free of the deposited protective film.

7. In a method of producing a gas sensor by forming at least two electrodes on an electrically insulating substrate by printing, depositing a sensitive layer to the tip portion of each of said electrodes and depositing a heat-resistant and electrically insulating protective film on a part of said sensitive layer and on a part of said each electrode, the improvement wherein said sensitive layer is formed by a method comprising the steps of forming a stoichiometrically metastable $TiO_{2-x}$ layer by plasma spraying on said electrically insulating substrate, and then heat-treating said $TiO_{2-x}$ film to form a diffusion reactive layer with said substrate and to form dispersedly fine grooves on the surface while at least the surface portion of said metastable $TiO_{2-x}$ layer is converted to stable titanium oxide ($TiO_2$).

8. The method of producing a gas sensor as defined in claim 7, wherein said $TiO_{2-x}$ layer is formed by plasma spraying titanium oxide on said substrate in an atmosphere of hydrogen and argon gas.

9. The method of producing a gas sensor as defined in claim 7, wherein said heat treating is effected in an atmosphere including oxygen gas.

10. The method of producing a gas sensor as defined in claim 7, wherein said heat treating is effected at a temperature of at least 1,000° C. and less than a melting point of said titanium oxide and the material of said substrate.

11. The gas sensor as defined in claim 1, wherein said substrate is of alumina, and said diffusion reactive layer is a solid solution of alumina and titania or a compound oxide of alumina and titania.

12. The gas sensor as defined in claim 1, wherein the titanium oxide is sprayed on the substrate at a sufficiently high temperature such that a diffusion reaction takes place between the substrate material and the titanium oxide.

13. The gas sensor as defined in claim 1, wherein the titanium oxide layer is a layer formed by plasma spraying.

14. The gas sensor as defined in claim 1, wherein said titanium oxide layer is stabilized titanium oxide.

15. The gas sensor as defined in claim 1, wherein the fine grooves or pores are uniformly dispersed in the surface portion of the titanium oxide layer.

16. A gas sensor comprising:
an electrically insulating substrate of thin plate;
electrodes provided on said substrate;
a sensitive layer of titanium oxide deposited by plasma spraying on one end portion of each of said electrodes and a part of said substrate adjacent to the end portions, the end portions of said electrodes being electrically connected to each other through said sensitive layer;
a heat-resistant and electrically insulating protective film provided to cover said electrodes;
wherein said sensitive layer includes a diffusion reactive layer formed at the boundary between said sensitive layer and said substrate, and further includes a surface portion, farthest from the diffusion reactive layer, formed with a plurality of grooves; and
wherein at least a part of each electrode covered with said sensitive layer is free of said protective layer.

17. The gas sensor as defined in claim 16, wherein said electrically insulating substrate of thin plate is made of alumina.

18. The gas sensor as defined in claim 17, wherein said sensitive layer is 10–100 $\mu$m thick and said diffusion reactive layer is 0.1–5 $\mu$m thick.

19. The gas sensor as defined in claim 18, wherein said substrate is a thin plate which is 0.4–0.6 mm thick.

20. A method of producing a gas sensor, which comprises the steps of:

forming, by printing, at least two electrodes spaced from each other on an electrically insulating substrate;
depositing a stoichiometrically metastable $TiO_{2-x}$ layer by plasma spraying powder of titanium oxide on said electrodes and said substrate so as to cover a tip portion of each of said electrodes and a part of said substrate adjacent to said tip portion and bridging between the electrodes;
heat-treating said $TiO_{2-x}$ layer in an atmosphere containing oxygen at a temperature of at least 1000° C. but less than the melting points of said titanium oxide and said substrate, to convert said $TiO_{2-x}$ layer to a stable titanium oxide ($TiO_2$) layer, and to form a diffusion reactive layer at the boundary between said sensitive layer and said substrate and a plurality of fine grooves on the surface of said sensitive layer farthest from said diffusion reactive layer; and
depositing a heat-resistant and electrically insulating protective film on a part of said sensitive layer and said electrodes so that a part of each electrode covered with said sensitive layer is free of said protective film.

21. The method as defined in claim 20, wherein said substrate is a thin plate of alumina.

22. The method as defined in claim 21, wherein said sensitive layer is 10–100 $\mu$m thick and said diffusion reactive layer is 0.1–5 $\mu$m thick.

23. The method as defined in claim 21, wherein said thin plate is 0.4–0.6 mm thick, said sensitive layer is 15–60 $\mu$m and said diffusion reactive layer is 0.8–1.2 $\mu$m.

24. The method as defined in claim 20, wherein said depositing a stoichiometrically metastable $TiO_{2-x}$ layer is performed in an atmosphere including hydrogen.

25. The method as defined in claim 20, wherein the metastable $TiO_{2-x}$ layer is deposited to have a thickness of 10–100 $\mu$m.

26. The method as defined in claim 20, wherein the heat-treating is performed at a temperature of at least 1080° C.

* * * * *